(12) United States Patent
Cooke et al.

(10) Patent No.: US 6,939,882 B1
(45) Date of Patent: Sep. 6, 2005

(54) FUNGICIDES

(75) Inventors: Tracey Cooke, St. Albans (GB); David Hardy, Cambridge (GB); Brian Anthony Moloney, Oxon (GB); Mary Josephine O'Mahony, Cambridge (GB); Michael George Pettett, Ongar (GB); Gita Patel, Cambridge (GB); Stefan Schnatterer, Hattersheim (DE)

(73) Assignee: Aventis Cropsciences GmbH (DE)

( * ) Notice: Subject to any disclaimer, the term of this patent is extended or adjusted under 35 U.S.C. 154(b) by 3 days.

(21) Appl. No.: 10/049,980

(22) PCT Filed: Aug. 11, 2000

(86) PCT No.: PCT/EP00/08268
§ 371 (c)(1),
(2), (4) Date: Sep. 3, 2002

(87) PCT Pub. No.: WO01/12604
PCT Pub. Date: Feb. 22, 2001

(30) Foreign Application Priority Data

Aug. 18, 1999 (GB) .............................. 9919558

(51) Int. Cl.$^7$ ..................... A01N 43/40; C07D 213/00
(52) U.S. Cl. ....................... 514/336; 514/311; 514/332; 514/340; 514/342; 514/357; 546/176; 546/255; 546/271.1; 546/278.7; 546/329; 546/332; 546/336
(58) Field of Search ................. 546/307, 330, 546/337, 357, 287, 336, 331; 514/357, 345, 353, 336, 311; 424/405

(56) References Cited

U.S. PATENT DOCUMENTS

| | | | | |
|---|---|---|---|---|
| 4,943,583 A | * | 7/1990 | Luthy | 514/364 |
| 6,432,964 B1 | * | 8/2002 | Atherall et al. | 514/260.1 |
| 6,503,933 B1 | * | 1/2003 | Moloney et al. | 514/357 |
| 6,541,630 B1 | * | 4/2003 | Atherall et al. | 544/278 |
| 6,630,495 B1 | * | 10/2003 | Cooke et al. | 514/357 |

FOREIGN PATENT DOCUMENTS

| | | |
|---|---|---|
| EP | 0270061 | 6/1988 |
| EP | 0287691 | 10/1988 |
| EP | 0288976 | 11/1988 |
| EP | 0350691 | 1/1990 |
| EP | 0469711 | 2/1992 |
| EP | 0573883 | 12/1993 |
| EP | 0577555 | 1/1994 |
| EP | 0648729 | 4/1995 |
| EP | 0648752 | 4/1995 |
| EP | 0882717 | 12/1998 |
| GB | 2068365 | 8/1981 |
| GB | 2307177 | 5/1997 |
| JP | 58-035174 | 3/1983 |
| JP | 1-131146 | 5/1989 |
| JP | 2-104575 | 4/1990 |
| JP | 4-005282 | 1/1992 |
| JP | 7-025853 | 1/1995 |
| WO | 92/07848 | 5/1992 |
| WO | 97/10215 | 3/1997 |
| WO | 98/42671 | 10/1998 |
| WO | 98/50352 | 11/1998 |
| WO | 99/07687 | 2/1999 |
| WO | 99/42447 | 8/1999 |

OTHER PUBLICATIONS

Leuthy, Christoph, AN 1988:524419, HCAPLUS, abstract of EP 270061.*

Minn, Klemens, "Chalcones Via A Palladium–Catalyzed Coupling of Iodoheterocycles to 1–phenyl–2–propyn–1–ol", *Chemical Abstracts Service*, Columbus, Ohio, Database Accession No. 115:8710 CA, XP002152591.

* cited by examiner

Primary Examiner—Sabiha N. Qazi
(74) Attorney, Agent, or Firm—Ostrolenk, Faber, Gerb & Soffen, LLP

(57) ABSTRACT

Use of compounds of general formula (I) or salts thereof as phytopathogenic fungicides wherein the various radicals and substituents are as defined in the description, pesticidal compositions containing them and method for combatting pests which comprises applying these.

2 Claims, No Drawings

FUNGICIDES

This invention relates to compounds having fungicidal activity.

As a prior art including compounds similar to the compound according to the invention in the chemical structure, there have hitherto been known the specification of EP0288976. It discloses that the compounds protect plants against attack by harmful microorganisms, for example phytopathogenic fungi, bacteria and viruses. Nevertheless, nothing is written about an eventual action of this sort of compounds on the metabolism phtyopatogen organisms.

In a first aspect the invention provides the use of a compound of general formula I or salts thereof as phytopathogenic fungicides

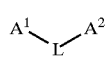 (I)

where
$A^1$ is 3-Cl-5-CF$_3$-2-pyridyl;
$A^2$ is optionally substituted heterocyclyl or optionally substituted carbocyclyl ($A^2$ is preferably phenyl, cyclohexyl, cyclopropyl or heterocyclyl, each of which may be substituted); excepted when L is —N(R$_3$)N(R$_4$)C(=O) or —CH$_2$OCH$_2$—, then $A_2$ can not contain any heterocyclyl containing N or O;
L is a 3-atom linker selected from the list: —CH(R$^1$)N(R$^3$)CH(R$^2$)—, —N(R$^3$)N(R$^4$)C(=X)—, —C(=X)N(R$^3$)CH(R$^1$)—, —CH(R$^1$)OC(=X)—, —CH(R$^1$)OCH(R$^2$)—, —N(R$^3$)C(=X)N(R$^4$)—, —C(R$^1$)=C(R$^2$)C(=X)—, —CH(R$^1$)N=C(R$^2$)—, —O—N=C(R$^1$)—, —O—N(R$^3$)C(=X)—, —N(R$^3$)N(R$^4$)CH(R$^1$), —N(R$^3$)C(Y)=N—, —N=C(Y)—N(R$^3$)—, —C(=X)—N(R$^3$)N(R$^4$)—, —C(Y)=N—N(R$^4$)— and —N(R$^3$)CH(R$^1$)C(=X)—; wherein $A^1$ is attached to the left hand side of linker L (L is preferably selected from the list: —CH(R$^1$)N(R$^3$)CH(R$^2$)—, —N(R$^3$)N(R$^4$)C(=X)—, —C(=X)N(R$^3$)CH(R$^1$), —CH(R$^1$)OC(=X)—, —CH(R$^1$)OCH(R$^2$)—, —N(R$^3$)C(=X)N(R$^4$)—, —C(R$^1$)=C(R$^2$)C(=X)—, —CH(R$^1$)N=C(R$^2$)—, —O—N=C(R$^1$)—, —O—N(R$^3$)C(=X)—);
where $R^1$ and $R^2$, which may be the same or different, are $R^b$, cyano, nitro, halogen, —OR$^b$, —SR$^b$ or optionally substituted amino ($R^1$ and $R^2$ are preferably hydrogen, acyl, optionally substituted alkyl, cyano or optionally substituted phenyl);
$R^3$ and $R^4$, which may be the same or different, are $R^b$, cyano or nitro ($R^3$ and $R^4$ are preferably hydrogen, acyl or optionally substituted alkyl);
or any $R^1$, $R^2$, $R^3$ or $R^4$ group, together with the interconnecting atoms, can form a 5- or 6-membered ring with any other $R^1$, $R^2$, $R^3$ or $R^4$, or any $R^1$, $R^2$, $R^3$ or $R^4$ group, together with the interconnecting atoms can form a 5- or 6-membered ring with $A^2$;
X is oxygen, sulfur, N—OR$^b$, N—R$^b$ or N—N(R$^b$)$_2$ (X is preferably oxygen or sulfur); and
Y is halogen, —OR$^b$, —SR$^b$, —N(R$^b$)$_2$, —NR$^b$(OR$^b$) or —NR$^b$N(R$^b$)$_2$;
wherein $R^b$ is alkyl, alkenyl, alkynyl, carbocyclyl or heterocyclyl, each of which may be substituted; or hydrogen or acyl, or two adjacent $R^b$ groups together with the nitrogen atom to which they are attached may form a 5- or 6-membered ring.

Preferred substituents on the 2-pyridyl group ($A^1$) are halogen, hydroxy, cyano, nitro, SF$_5$, trialkylsilyl, optionally substituted amino, acyl, or a group —R$^a$, —OR$^a$ or —SR$^a$, or a group —C(R$^a$)=N-Q, where Q is —R$^a$, —OR$^a$, —SR$^a$ or optionally substituted amino, wherein R$^a$ is alkyl, alkenyl, alkynyl, carbocyclyl or heterocyclyl, each of which may be substituted; or two adjacent substituents together with the atoms to which they are attached form an optionally substituted ring which can contain up to 3 hetero atoms. Especially preferred substituents are alkoxy, alkyl, cyano, halogen, nitro, alkoxycarbonyl; alkylsulfinyl, alkylsulfonyl and trifluoromethyl, particularly chlorine and trifluoromethyl.

Preferably, the 2-pyridyl group is substituted at the 3 and/or 5 position.

The invention also includes any of the compounds specifically exemplified hereinafter.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carton atoms and may contain up to 3 double or triple bonds which may be conjugated, for example vinyl, allyl, butadienyl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 5 to 7 ring-atoms up to 4 of which may be hetero-atoms such as nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxy; mercapto; azido; nitro; halogen; cyano; acyl; optionally substituted amino; optionally substituted carbocyclyl; optionally substituted heterocyclyl; cyanato; thiocyanato; —SF$_5$; —OR$^a$; —SR$^a$ and —Si(R$^a$)$_3$, where R$^a$ is alkyl, alkenyl, alkynyl, carbocyclyl or heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocyclyl or heterocyclyl group the list includes a divalent group such as oxo or imino, which may be substituted by optionally substituted amino, $R^a$ or —$OR^a$. Preferred groups are oxo, imino, alkylimino, oximino, alkyloximino or hydrazono.

Any amino group, when substituted and where appropriate, may be substituted by one or two substituents which may be the same or different, selected from the list: optionally substituted alkyl, optionally substituted amino, —$OR^8$ and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulfur and phosphorus-containing acids as well as carboxylic acids. Typically the residues are covered by the general formulae —$C(=X^a)R^c$, —$S(O)_pR^c$ and —$P(=X^a)(OR^a)(OR^a)$, where appropriate $X^a$ is O or S, $R^c$ is as defined for $R^a$, —$OR^a$, —$SR^a$, optionally substituted amino or acyl; and p is 1 or 2. Preferred groups are —$C(=O)R^d$, —$C(=S)R^d$, and —$S(O)_pR^d$ where $R^d$ is alkyl, $C_1$ to $C_5$ alkoxy, $C_1$ to $C_5$ alkylthio, phenyl, heterocyclyl or amino, each of which may be substituted.

Complexes of compounds of the invention are usually formed from a salt of formula $MAn_2$, in which M is a divalent metal cation, e.g. copper, manganese, cobalt, nickel, iron or zinc and An is an anion, e.g. chloride, nitrate or sulfate.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers, the invention includes individual isomers as well as mixtures thereof.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botryis cinerea*), damping off (*Rhizoctonia solani*), wheat brown rust (*Puccinia recondita*), late tomato or potato blight (*Phytophthora infestans*), apple scab (*Venturia inaequalis*), and glume blotch (*Leptosphaeria nodorum*). Other fungi against which the compounds may be active include other powdery mildews, other rusts, and other general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid: an N-acylsarcosinate; mono- or di-esters of phosphoric acid with fatty alcohol ethoxylates or alkyl phenol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine; the dialkyl sulfosuccinates, e.g. the sodium sulfonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; is alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystalisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compound of the invention dissolved in a water-immiscible solvent which forms an emulsion or microemulsion on addition to water in the presence of an emulsifying agent.

A granular solid comprises a compound of the invention associated with similar diluents to those that may be employed in dusting powders, but the mixture is granulated by known methods. Alternatively it comprises the active ingredient absorbed or coated on a pre-formed granular carrier, for example, Fuller's earth, attapulgite, silica or limestone grit.

Wettable powders, granules or grains usually comprise the active ingredient in admixture with suitable surfactants and an inert powder diluent such as clay or diatomaceous earth.

Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

The invention is generally applied to seeds, plants or their habitat Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth, as this is the time when the plant can be most severely damaged. The spray or dust can conveniently contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications. Also the compounds of the invention can be used to treat insect and fungus infestations in domestic and farm animals.

Compounds of the invention may be prepared, in known manner, in a variety of ways.

Compounds of formula Iai, i.e. compounds of general formula I where L is —CH(R$^1$)NHCH(R$^2$)—, may be prepared according to reaction scheme 1. Compounds of formula II or their hydrochloride salts can be condensed with compounds of formula III and the intermediate reduced with a suitable reagent such as sodium cyanoborohydride to give compounds of formula Iai.

Scheme 1

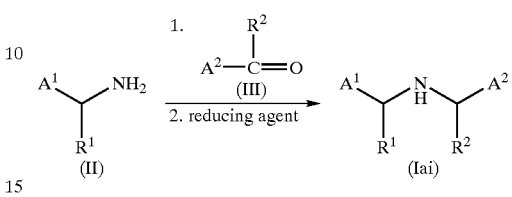

Compounds of formula II may be prepared by methods described in international application PCT/GB/99/00304.

Compounds of formula Iai may also be prepared by reacting compounds of formula IV with compounds of formula V in the same manner as above (Scheme 2).

Scheme 2

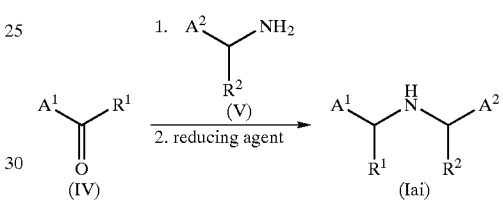

Compounds of formula Iaii, i.e. compounds of general formula I where L is —CH(R$^1$)N(R$^3$)CH(R$^2$) and R$^3$ is not hydrogen, may be prepared by reacting compounds of formula Iai with a base and R$^3$Q, where Q is a leaving group such as a halogen. A suitable base is triethylamine (Scheme 3).

Scheme 3

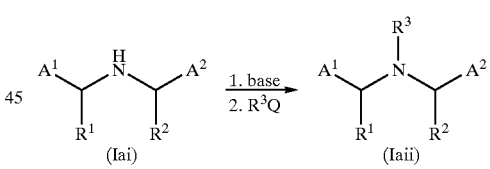

Compounds of formula Ib, i.e. compounds of general formula I where L is —N(R$^3$)N(R$^4$)C(=X)—, may be prepared according to reaction scheme 4 by reacting compounds of formula VI with compounds of formula VII, where Q is a leaving group such as halogen, preferably chlorine. A preferred base is triethylamine.

Scheme 4

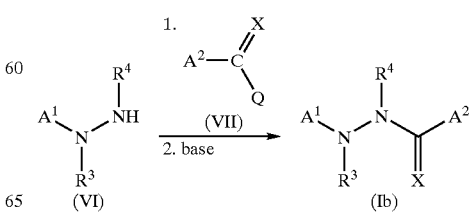

Compounds of formula Ic, i.e. compounds of general formula I where L is —C(═O)N(R³)CH(R¹), may be prepared by radical bromination of compounds of formula VIII, followed by reaction of these intermediates with compounds of formula IX according to scheme 5. Preferred reaction conditions are irradiation of a solution of VIII in carbon tetrachloride in the presence of N-bromosuccinimide and a catalytic amount of 2,2'-azobisisobutyronitrile, followed by addition of IX.

Scheme 5

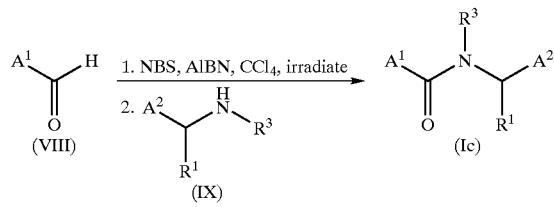

Compounds of formula Id, i.e. compounds of general formula I where L is —CH(R¹)O(C═O)—, may be prepared according to reaction scheme 6 by formation of the cesium salt of is compounds of formula XI, followed by reaction with compounds of formula X where Q is a suitable leaving group, such as chlorine.

Scheme 6

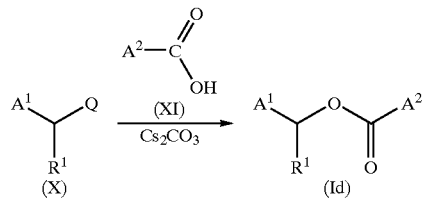

Compounds of formula Ie, i.e. compounds of general formula I where L is —CH(R¹)OCH(R²)—, may be prepared by reaction of compounds of formula XII with a suitable base such as sodium hydride, followed by reaction of the resulting anion with compounds of formula X, where Q is a suitable leaving group such as halogen, according to reaction scheme 7.

Scheme 7

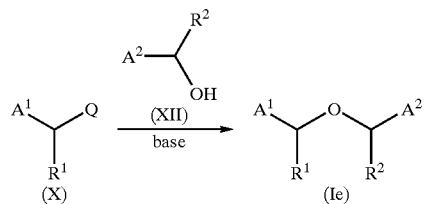

Compounds of formula If, i.e. compounds of general formula I where L is —N(R³)C(═X)N(R⁴) and X is O or S, may be prepared according to reaction scheme 8 by reaction of compounds of formula XIII with compounds of formula XIV, where X is O or S, followed by the addition of compounds of formula XV. The order of addition of compounds of formulae XIII and XV may be reversed.

Scheme 8

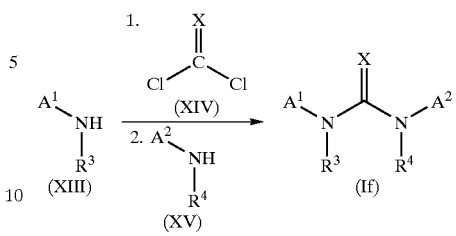

Compounds of formula Ig, i.e. compounds of general formula I where L is —C(R¹)═C(R²)C(═O)—, may be prepared according to reaction scheme 9 by reaction of compounds of formula XVI with compounds of formula XVII in the presence of sodium hydroxide.

Scheme 9

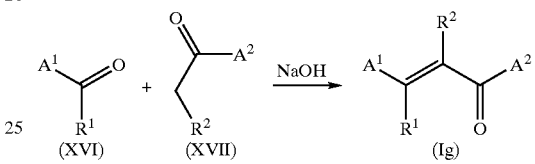

Compounds of formula Ih, i.e. compounds of general formula I where L is —C(R¹)═N—N(R³)—, may be prepared by reacting compounds of formula XVIII with compounds of formula XIX according to reaction scheme 10.

Scheme 10

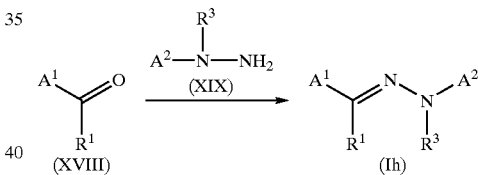

Compounds of formula Ii, i.e. compounds of general formula I where L is —CH(R¹)N═C(R²)—, may be prepared according to reaction scheme 11 by reacting compounds of formula XX with a base, followed by reaction with compounds of formula XXI, where Q is a suitable leaving group, preferably chlorine. A suitable base is sodium hydride. Compounds of formula XX are known or can be prepared in a known manner by a is skilled chemist.

Scheme 11

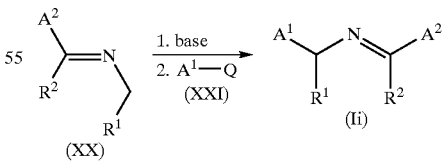

Compounds of formula Ij, i.e. compounds of general formula I where L is —O—N═C(R¹)—, may be prepared according to reaction scheme 12 by the reaction of compounds of formula XXII with a base, followed by reaction with compounds of formula XXI, where Q is a suitable leaving group, preferably chlorine. A suitable base is sodium hydride.

Scheme 12

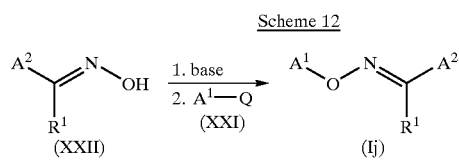

Compounds of formula XXII may be prepared according to reaction scheme 13.

Scheme 13

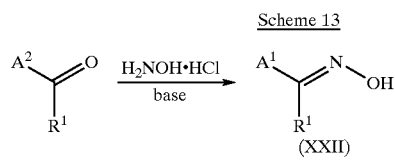

Compounds of formula Imi, i.e. compounds of general formula I where L is —O—NHC(=O)—, may be prepared according to reaction scheme 14 by the reaction of compounds of formula XXIII with compounds of formula XXIV, where Q is a suitable leaving group.

Scheme 14

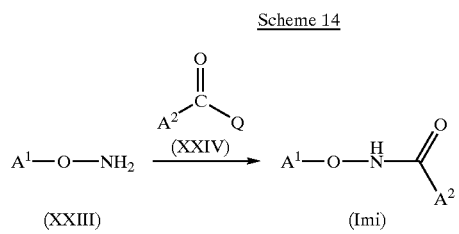

Compounds of formula XXIV can be prepared from the corresponding hydroxy compounds by methods known to the skilled chemist. Compounds of formula XXIV can be isolated and used according to scheme 14 or generated in situ and used without isolation. A typical method, known to the skilled chemist, uses carbonyldiimidazole to generate compounds of formula XXIV in situ.

Compounds of formula XXIII can be prepared according to reaction scheme 15.

Scheme 15

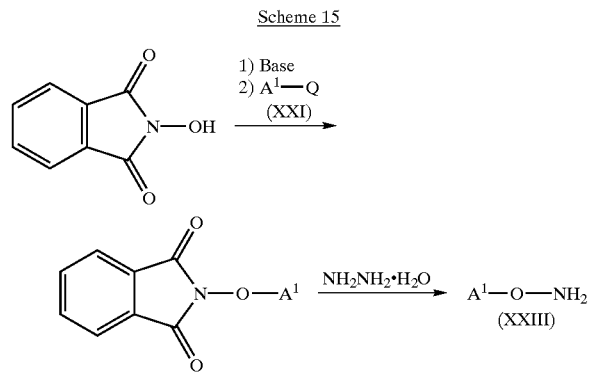

Compounds of formula Imii, i.e. compounds of general formula I where L is —N($R^3$)C(=O)— wherein $R^3$ is not hydrogen, may be prepared by reaction of compounds of formula Imi with a base, followed by reaction with $R^3Q$, where Q is a suitable leaving group, such as a halogen. A suitable base is potassium tert-butoxide (Scheme 16).

Scheme 16

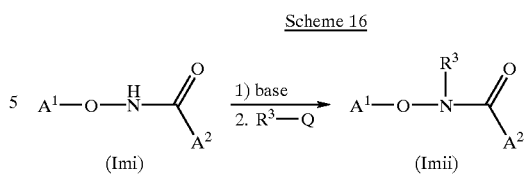

Other methods will be apparent to the chemist skilled in the art, as will be the methods for preparing starting materials and intermediates.

Collections of compounds of formula I may also be prepared in a parallel manner, either manually, automatically or semi-automatically. This parallel preparation may be applied to the reaction procedure, work-up or purification of products or intermediates. For a review of such procedures see by S. H. DeWitt in "Annual Reports in Combinatorial Chemistry and Molecular Diversity: Automated synthesis", Volume 1, Verlag Escom 1997, pages 69 to 77.

Furthermore, compounds of the formula I may be prepared using solid-supported methods, where the reactants are bound to a synthetic resin. See for example: Barry A. Bunin in "The Combinatorial Index", Academic Press, 1998 and "The tea-bag method" (Houghten, U.S. Pat. No. 4,631, 211; Houghten et al., Proc. Natl. Acad. Sci, 1985, 82, 5131–5135).

The invention is illustrated in the following Examples. Structures of isolated, novel compounds were confirmed by NMR and/or other appropriate analyses.

EXAMPLE 1

N-(2-Chlorobenzyl)-N-{1-[3-chloro-5-(trifluorormethyl)-2-pyridyl]ethyl}amine
(Compound 27)

α-Methyl-[3-chloro-5-(trifluoromethyl)-2-pyridyl] methylamine (0.2 g) was dissolved in trimethylorthoformate (10 ml) and triethylamine (0.22 ml) was added. After 5 minutes 2-chlorobenzaldehyde (0.26 g) was added and the resulting mixture stirred for 3.5 hours at room temperature to give a precipitate. Sodium cyanoborohydride (1.5 ml, 0.1 M solution in tetahydrofuran) and acetic acid (0.1 ml) were then added and the mixture stirred for 16 hours at room temperature. Brine (5 ml) and water (10 ml) were then added and the mixture stirred for 20 minutes. The phases were separated and the organic phase evaporated. The residue was purified by silica gel chromatography to give the title product, m.p. 117° C.

EXAMPLE 2

N-{[3-Chloro-5-(trifluoromethyl)-2-pyridyl]
methyl}-N-[1-(3,4-difluorophenyl)-ethyl]amine
(Compound 23)

Triethylamine (0.08 ml) and 1-(3,4-difluorophenyl)-1-ethagamine (0.11 g) were dissolved in trimethylorthoformate (10 ml), 3-Chloro-(5-trifluoromethyl)-pyridine-2-carboxaldehyde (0.15 g) was added and the solution stirred for 4 hours at room temperate. Sodium cyanoborohydride (1 ml, 0.1 M solution in tetahydrofuran) and acetic acid (0.07 ml) were then added and the mixture stirred for 16 hours at room temperature. Brine (5 ml) and water (10 ml) were then added and the mixture stirred for 20 minutes. The phases were separated and the organic phase evaporated. The crude material was purified by silica gel chromatography to give the title product, $^1$H N.M.R (CDCl$_3$) δ(ppm) 1.4 (3H, d), 2.6

(1H, broad s), 3.8 (1H, q), 3.9 (1H, s), 7.1–7.3 (3H, m), 7.9 (1H, s) and 8.8 (1H, s).

EXAMPLE 3

Ethyl 2-[acetyl(benzyl)amino]-2-[3-chloro-5-trifluoromethyl)-2-pyridyl]acetate (Compound 4)

To a solution of compound 1 (0.6 mmol) in diethyl ether was added triethylamine (0.7 mmol) followed by acetyl chloride in diethyl ether (0.7 mmol). The mixture was stirred for two hours at room temperature before the addition of hydrochloric acid (8 ml, 2M). The organic phase was isolated, washed with sodium bicarbonate (10 ml), dried over magnesium sulfate and evaporated to yield the title compound, $^1$H N.M.R (CDCl$_3$)(ppm) δ1.2 (3H, t), 2.3 (3H, s), 4.2 (2H, q), 4.8 (2H, q), 6.8–7.1 (6H, m), 7.5 (1H, s) and 8.5 (1H, s).

The following compounds of formula Iz (see Table A), i.e. compounds of general formula I where $A^1$ is 3-Cl-5-CF$_3$-2-pyridyl and L is —CH(R$^1$)N(R$^3$)CH(R$^2$)—, may be prepared by methods analogous to those of Examples 1, 2 and 3. The amine starting materials were obtained using methods described in international application PCT/GB/99/00304.

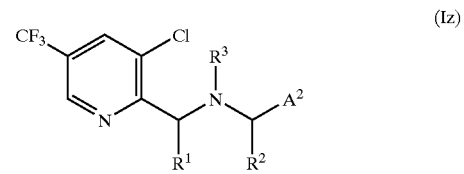

(Iz)

TABLE A

| Cmp | R$^1$ | R$^2$ | R$^3$ | A$^2$ | m.p./° C. |
|---|---|---|---|---|---|
| 1 | EtOC(=O)— | H | H | phenyl | oil |
| 2 | EtOC(=O)— | H | H | 2-Cl-phenyl | oil |
| 3 | EtOC(=O)— | H | H | 3,4-methylenedioxyphenyl | oil |
| 4 | EtOC(=O)— | H | MeC(=O)— | phenyl | oil |
| 5 | EtOC(=O)— | H | MeOCH$_2$C(=O)— | phenyl | oil |
| 6 | EtOC(=O)— | H | MeOC(=O)—C(=O)— | phenyl | 104–7 |
| 7 | EtOC(=O)— | H | MeC(=O)— | 2-Cl-phenyl | 77–81 |
| 8 | EtOC(=O)— | H | MeOCH$_2$C(=O)— | 2-Cl-phenyl | oil |
| 9 | EtOC(=O)— | H | MeOC(=O)—C(=O)— | 2-Cl-phenyl | 128–31 |
| 10 | EtOC(=O)— | H | MeC(=O)— | 3,4-methylenedioxyphenyl | oil |
| 11 | EtOC(=O)— | H | MeOCH$_2$C(=O)— | 3,4-methylenedioxyphenyl | oil |
| 12 | EtOC(=O)— | H | MeOC(=O)—C(=O)— | 3,4-methylenedioxyphenyl | 106–9 |
| 13 | H | MeOC(=O)CH$_2$— | H | phenyl | oil |
| 14 | H | EtOC(=O)CH$_2$— | H | phenyl | oil |
| 15 | H | H | H | phenyl | oil |
| 16 | H | H | H | 2-Cl-6-F-phenyl | oil |
| 17 | H | Me | H | 2-Cl-phenyl | oil |
| 18 | H | Me | H | 2,6-diF-phenyl | oil |
| 19 | H | Me | H | *(benzodioxane structure)* | oil |
| 20 | H | Me | H | 4-tolyl | oil |
| 21 | H | H | H | 2,5-diF-phenyll | oil |
| 22 | H | Me | H | 4-NO$_2$-phenyl | oil |
| 23 | H | Me | H | 3,4-diF-phenyl | oil |
| 24 | H | H | H | 2-Cl-phenyl | oil |
| 25 | H | H | H | 4-PhO-phenyl | oil |
| 26 | H | H | H | 2-NO$_2$-phenyl | oil |
| 27 | Me | H | H | 2-Cl-phenyl | 117 |
| 28 | Me | H | H | 2-NO$_2$-phenyl | 136 |
| 29 | H | Me | H | phenyl | oil |
| 30 | H | Me | H | 3-CF$_3$O-phenyl | oil |
| 31 | H | Me | H | 4-CF$_3$O-phenyl | oil |
| 32 | H | Me | H | *(tetrahydronaphthalene structure)* | oil |
| 33 | H | Me | H | 4-Cl-phenyl | oil |
| 34 | H | Me | H | 4-Br-phenyl | oil |
| 35 | Me | H | H | cyclohexyl | oil |
| 36 | Me | H | H | 2-F-phenyl | oil |
| 37 | Me | H | H | 4-Cl-phenyl | oil |
| 38 | Me | H | H | 2,5-diMeO-phenyl | oil |
| 39 | Me | H | H | 2-Cl-6-F-phenyl | oil |
| 40 | Me | H | H | 2-Br-phenyl | oil |
| 41 | Me | H | H | 3-CF$_3$O-phenyl | oil |
| 42 | Me | H | H | 4-MeS-phenyl | oil |

TABLE A-continued

| Cmp | R¹ | R² | R³ | A² | m.p./° C. |
|---|---|---|---|---|---|
| 43 | Me | H | H | 2,5-xylyl | oil |
| 44 | H | H | H | cyclohexyl | oil |
| 45 | H | H | H | 3-Br-phenyl | oil |
| 46 | H | H | H | 4-Me₂N-phenyl | oil |
| 47 | H | H | H | 4-Cl-phenyl | oil |
| 48 | H | H | H | 2-F-phenyl | oil |
| 49 | H | H | H | 2,5-diMeO-phenyl | oil |
| 50 | H | H | H | 2-Br-phenyl | oil |
| 51 | H | H | H | 4-NO₂-phenyl | oil |
| 52 | H | H | H | 2,5-xylyl | oil |
| 53 | H | Me | H | (benzodioxole-methyl structure) | oil |
| 54 | H | H | H | pentaF-phenyl | oil |

The $^1$H N.M.R. or mass spectral data of those compounds in Table A which were not solid at room temperature are presented below.

Compound 1
$^1$H N.M.R (CDCl₃) δ (ppm) 1.2 (3H, t), 2.9 (1H broad s), 3.8 (1H, q), 4.2 (2H m), 5.0 (1H, s), 7.4–7.2 (5H, m), 7.9 (1H, s), 8.7 (1H, s).

Compound 2
$^1$H N.M.R (CDCl₃) δ (ppm) 1.2 (3H, t), 3.1 (1H, broad s), 4.0 (2H, q), 4.2 (2H, m), 5.1 (1H, s), 7.5–7.2 (4H, m), 8.0 (1H, s), 8.7 (1H, s).

Compound 3
$^1$H N.M.R (CDCl₃) δ (ppm) 1.2 (3H, t), 2.4 (1H, broad s), 3.8 (2H, q), 4.2 (2H, m), 5.0 (1H, s), 5.9 (2H, s), 6.74 (1H, d), 6.76 (1H, s), 6.83 (1H, s), 7.9 (1H, s), 8.7 (1H, s).

Compound 4
$^1$H N.M.R (CDCl₃) δ (ppm) 1.2 (3H, t), 2.3 (3H, s), 4.2 (2H, q), 4.8 (2H, q), 6.8–7.1 (6H, m), 7.5 (1H, s), 8.5 (1H, s).

Compound 5
m/z (APCI) 445 (M+H)⁺.

Compound 8
m/z (APCI) 479 (M+H)⁺.

Compound 10
m/z (APCI) 487 (M⁻).

Compound 11
m/z (APCI) 459 (M+H)⁺.

Compound 13
$^1$H N.M.R (CDCl₃) δ(ppm) 2.7 (1H, dd), 2.9 (1H, dd), 3.6 (3H, s), 3.9 (2H, s), 4.2 (1H, m), 7.3 (5H, m), 7.8 (1H, s), 8.8 (1H, m).

Compound 14
$^1$H N.M.R (CDCl₃) δ(ppm) 1.2 (3H, t), 2.7 (1H, dd), 2.8 (1h, dd), 3.9 (2H, s), 4.1 (2H, q), 4.2 (1H, m), 7.2–7.4 (5H, m), 7.8 (1H, s), 8.8 (1H, s).

Compound 15
$^1$H N.M.R (CDCl₃) δ(ppm) 4.2 (2H, s), 5.3 (2H, s), 7.3 (6H, m), 8.8 (1H, s), 8.9 (1H, s).

Compound 16
$^1$H N.M.R (CDCl₃) δ(ppm) 2.7 (1H, broad s), 4.05 (4H, s), 6.9–7.2 (3H, m), 7.8 (1H, s), 8.6 (1H, s).

Compound 17
$^1$H N.M.R (CDCl₃) δ(ppm) 1.4 (3H, d), 2.5 (1H, broad s), 3.9 (2H, m), 4.3 (1H, q), 7.1–7.3 (3H, m) 7.5 (1H, m) 7.8 (1H, s), 8.7 (1H, s).

Compound 18
$^1$H N.M.R (CDCl₃) δ(ppm) 1.5 (3H, d), 2.6 (1H, broads), 3.8 (1H, m), 4.0 (1H, m) 4.3 (1H, q), 6.8 (2H, m) 7.1 (1H, m) 7.8 (1H, s) 8.6 (1H, s).

Compound 19
$^1$H N.M.R (CDCl₃) δ(ppm) 1.4 (3H, d) 2.6 (1H, broad s), 3.8 (1H, q), 4.0 (2H, s), 4.3 (4H, s) 6.8 (2H, s), 6.9 (1H s), 7.9 (1H, s), 8.7 (1H, s).

Compound 20
$^1$H N.M.R (CDCl₃) δ(ppm) 1.5 (3H, d), 2.4 (3H, s), 2.8 (1H, broad s), 3.8 (1H, q), 4.0 (2H, m), 7.2 (2H, d), 7.3 (2H, d), 7.8 (1H, s), 8.7 (1H, s).

Compound 21
$^1$H N.M.R (CDCl₃) δ(ppm) 2.5 (1H, broad s), 4.0 (2H, s), 4.1 (2H, s), 6.8 (2H, m), 7.2 (1H, m), 7.8 (1H, s), 8.6 (1H, s).

Compound 22
$^1$H N.M.R (CDCl₃) δ(ppm) 1.4(3H, d), 2.5 (1H, broad s), 3.86 (2H, s), 3.9 (1H, m), 7.5 (2H, d), 7.8 (1H, s), 8.1 (2H, d), 8.7 (1H, s).

Compound 23
$^1$H N.M.R (CDCl₃) δ(ppm) 1.4 (3H, d), 2.6(1H, broad s), 3.8(1H, q), 3.9(1H, s), 7.1–7.3 (3H, m), 7.9(1H, s), 8.8 (1H, s).

Compound 24
$^1$H N.M.R (CDCl₃) δ(ppm) 4.1(4H, m), 4.4(1H, dd), 4.6(1H, dd), 6.5(1H, broads), 7.2–7.4(5H, m), 7.8 (1H, s), 8.6(1H, s).

Compound 25
$^1$H N.M.R (CDCl₃) δ(ppm) 3.9 (1H, dd), 4.2 (1H, dd), 4.4 (2H, m), 6.0 (1H, broad s), 6.9–7.0 (5H, m), 7.2–7.4 (4H, m), 8.0 (1H, s), 8.7 (1H, s).

Compound 26
$^1$H N.M.R (CDCl₃) δ(ppm) 4.3 (2H, m), 4.7 (2H, m), 7.0 (1H, broad s), 7.6 (1H, m), 7.7 (21, m), 7.9 (1H, s), 8.2 (1H, m), 8.6 (1H, s).

Compound 29
$^1$H N.M.R (CDCl₃) δ(ppm) 1.5 (3H, s), 2.6 (1H, broad s), 3.9 (1H, q), 4.0 (2H, s), 7.2–7.4 (5H, m), 7.8 (1H, s), 8.7 (1H, s).

Compound 30
$^1$H N.M.R (CDCl₃) δ(ppm) 1.4 (3H, d), 2.6 (1H, broad s), 3.8 (1H, q), 3.9 (2H, s), 4.0 (2H, s), 7.0(1H, m), 7.2–7.3 (3H, m), 7.8(1H, s), 8.7 (1H, s).

Compound 31
$^1$H N.M.R (CDCl₃) δ(ppm) 1.5 (3H, d), 2.7 (1H, broad s), 3.8 (1H, q), 6.5 (1H, m), 7.1 (2H, d), 7.4 (2H, d), 7.9 (1H, s), 8.8 (1H, s).

Compound 32
$^1$H N.M.R (CDCl₃) δ(ppm) 1.5 (3H, d), 1.8 (41, m), 2.8 (4H, m), 3.8 (1H, q), 4.0 (2H, s), 7.1 (3H, m), 7.9 (1H, s), 8.8 (1H, s).

Compound 33
¹H N.M.R (CDCl₃) δ(ppm) 1.42 (3H, d), 2.62 (1H, broad, s), 3.83 (1H, q), 3.92 (2H, s), 7.3 (4H, s), 7.82 (1H, s); 8.75 (1H, s).

Compound 34
¹H N.M.R (CDCl₃) δ(ppm) 1.42 (3H, d), 2.58 (1H, s, broad), 3.82 (1H, q), 3.92 (2H, s), 7.25 (2H, m), 7.45 (2H, m), 7.85 (1H, s), 8.72 (1H, s).

Compound 35
¹H N.M.R (CDCl₃) δ(ppm) selected peaks at 1.38(3H, d), 4.35 (1H, q), 7.85 (1H, s), 8.75 (1H, s).

Compound 36
¹H N.M.R (CDCl₃) δ(ppm) 1.38 (3H, d), 2.35 (1H, broad, s), 3.68 (2H, m), 4.42 (1H, q), 6.95 (1H, m), 7.05 (1H, m), 7.16 (1H, m), 7.32 (1H, m), 7.82 (1H, s), 8.75 (1H, s).

Compound 37
¹H N.M.R (CDCl₃) δ(ppm) selected peaks at 1.38 (3H, d), 3.56 (2H, m), 4.4 (1H, q), 7.88 (1H, s), 8.78 (1H, s).

Compound 39
¹H N.M.R (CDCl₃) δ(ppm) 1.3 (3H, d), 2.7 (1H, broad, s), 3.8 (2H, s), 4.4 (1H, q), 6.75 (1H, m), 6.98(2H, m), 7.72(1H, s), 8.55(1H, s).

Compound 40
¹H N.M.R (CDCl₃) δ(ppm) 1.41 (3H, d), 2.3 (1H, broad, s), 3.72 (2H, m), 4.25 (1H, q), 7.05–7.5 (4H, m), 7.85 (1H, s), 8.75 (1H, s).

Compound 41
¹H N.M.R (CDCl₃) δ(ppm) 1.38 (3H, d), 2.4 (1H s, broad), 3.6 (21, m), 4.4 (1H, q), 7.05–7.5 (4H, m), 7.88 (1H, s), 8.78 (1H, s).

Compound 42
¹H N.M.R (CDCl₃) δ(ppm) 1.38 (3H, d), 2.48 (3H, s), 3.6 (2H, m), 4.45 (1H, q), 7.2 (4H, m), 7.88 (1H, s), 8.78 (1H, s).

Compound 43
¹H N.M.R (CDCl₃) δ(ppm) 1.4 (3H, d), 2.25 (3H, s), 2.32 (3H, s), 2.5 (1H, broad, s), 3.58 (2H, m), 4.48 (1H, q), 6.9–7.08 (3H, m), 7.9 (1H, s), 8.78 (1H, s).

Compound 44
¹H N.M.R (CDCl₃) δ(ppm) selected peaks at 2.53 (2H, d), 4.1 (2H, s), 7.85 (1H, s), 8.75 (1H, s).

Compound 45
¹H N.M.R (CDCl₃) δ(ppm) selected peaks at 3.85 (1H, s), 4.1 (1H, s), 7.9 (1H, s), 8.75 (1H, s).

Compound 46
¹H N.M.R (CDCl₃) δ(ppm) selected peaks at 7.8 (1H, s), 8.68 (1H, s), 3.5 (1H, m), 3.9 (2H, m), 4.1 (1H, m).

Compound 47
¹H N.M.R (CDCl₃) δ(ppm) selected peaks at 3.86 (2H, s), 4.08 (2H, s), 7.90 (1H, s), 8.72(1H, s).

Compound 48
¹H N.M.R (CDCl₃) δ(ppm) 2.65 (1H, s, broad), 3.98 (2H, s), 4.15 (2H, s), 7.9 (1H, s), 8.75 (1H, s).

Compound 49
¹H N.M.R (CDCl₃) δ(ppm) selected peaks at 3.80 (3H, s), 3.85 (3H, s), 6.88 (2H, m), 7.06 (1H, m), 7.90 (1H, s), 8.72 (1H, s).

Compound 50
¹H N.M.R (CDCl₃) δ(ppm) selected peaks at 4.0 (2H, s), 4.1 (2H, s), 7.85 (1H, s), 8.70 (1H, s).

Compound 51
¹H N.M.R (CDCl₃) δ(ppm) selected peaks at 2.65 (1H, broad, s), 3.83 (2H, s), 4.0 (2H, s), 7.8 (1H, s), 8.65 (1H, s).

Compound 52
¹H N.M.R (CDCl₃) δ(ppm) selected peaks at 3.83 (2H, s), 4.18 (2H, s), 7.9 (1H, s), 8.75 (1H, s).

Compound 53
¹H N.M.R (CDCl₃) δ(ppm) 1.4 (3H, d), 2.5 (1H, broad s), 3.8 (1H, q), 3.9 (2H, s), 6.0 (2H, s), 6.8–6.9 (3H, m), 7.9 (1H, s), 8.7 (1H, s).

Compound 54
¹H N.M.R (CDCl₃) δ(ppm) selected peaks at 7.75 (1H, s), 8.80 (1H, s).

EXAMPLE 4

N'-1-[3-Chloro-5-(trifluoromethyl)-2-pyridyl-2,6-dichloro-1-benzenecarbohydrazide (Compound 102)

3-Chloro-5-trifluoromethyl)pyrid-2-ylhydrazine (0.32 g) was dissolved in dichloromethane (7 ml) and treated dropwise with 2,6-dichlorobenzoyl chloride (0.31 g) in dichloromethane (2 ml). Triethylamine (0.15 g) was then added and the reaction stirred at room temperature overnight. The organic solution was washed sequentially with sodium bicarbonate solution and brine and evaporated to give a solid. The residue was purified by trituration (dichloromethane) to give the title compound, m.p. 212–5° C.

The following compounds of formula Iy (see Table B), i.e. compounds of general formula I where L is —N(R³)NHC(=O)—, may be prepared by methods analogous to those of Example 4.

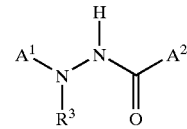

(Iy)

TABLE B

| Cmp | A¹ | R³ | A² | m.p./° C. |
|---|---|---|---|---|
| 101 | 3-Cl-5-CF₃-pyridyl | H | 2-Cl-phenyl | 168-70 |
| 102 | 3-Cl-5-CF₃-pyridyl | H | 2,6-diCl-phenyl | 212-5 |
| 103 | 3-Cl-5-CF₃-pyridyl | H | 2-NO₂-phenyl | 182-3 |
| 104 | 3-Cl-5-CF₃-pyridyl | H | 2,6-diMeO-phenyl | 204-6 |
| 105 | 3-Cl-5-CF₃-pyridyl | H | 2-tolyl | 168-9 |
| 107 | 3-Cl-5-CF₃-pyridyl | H | cyclopropyl | 152-4 |
| 108 | 3-Cl-5-CF₃-pyridyl | H | cyclohexyl | 111-4 |
| 109 | 3-Cl-5-CF₃-pyridyl | Me | 2,6-diCl-phenyl | 219-20 |
| 110 | 3-Cl-5-CF₃-pyridyl | Me | 2-NO₂-phenyl | 198-9 |
| 111 | 3-Cl-5-CF₃-pyridyl | Me | 2,6-diMeO-phenyl | 234-6 |
| 112 | 3-Cl-5-CF₃-pyridyl | Me | 2-tolyl | 202-4 |
| 113 | 3-Cl-5-CF₃-pyridyl | Me | 2-Cl-6-F-phenyl | 207-8 |
| 115 | 3-Cl-5-CF₃-pyridyl | Me | cyclopropyl | 159-60 |
| 116 | 3-Cl-5-CF₃-pyridyl | Me | cyclohexyl | 216-9 |
| 117 | 5 Cl-3-CF₃-pyridyl | H | 2,6-diCl-phenyl | 199-203 |
| 118 | 5-Cl-3-CF₃-pyridyl | H | 2-NO₂-phenyl | 156-8 |
| 119 | 5-Cl-3-CF₃-pyridyl | H | 2,6-diMeO-phenyl | 194-5 |
| 120 | 5-Cl-3-CF₃-pyridyl | H | 2-tolyl | 180-1 |
| 121 | 5-Cl-3-CF₃-pyridyl | H | 2-Cl-6-F-phenyl | 173-5 |
| 123 | 5-Cl-3-CF₃-pyridyl | H | cyclopropyl | 143-5 |
| 124 | 5-Cl-3-CF₃-pyridyl | H | cyclohexyl | 121 |
| 125 | 3-Cl-5-CF₃-pyridyl | H | 2,3,6-triF-phenyl | 154-6 |
| 126 | 3-Cl-5-CF₃-pyridyl | H | 2-Cl-6-F-phenyl | 192 |

EXAMPLE 5

N-2-(Phenylethyl)-3-chloro-5-(trifluoromethyl)-2-pyridinecarboxamide (Compound 206)

3-Chloro-(5-trifluoromethyl)pyridine-2-carboxaldehyde (0.15 g) was dissolved in carbon tetrachloride (10 ml), 2'-Azobisisobutyronitrile (0.002 g) and N-bromosuccinimide (0.16 g) were added and the mixture was heated to reflux using a sun lamp. After 45 minutes the solution was cooled down to 0° C. (R)-(+)-α-methylbenzylamine (0.09 g) in carbon tetrachloride (0.03 ml) was added and stirred for 20 minutes at 0° C., then for 3 hours at room temperature. The mixture was diluted with dichloromethane and washed with water. The organic layer was isolated, dried over magnesium sulphate and evaporated to give the crude compound. The crude material was purified by silica gel chromatography to give the title product, m.p. 88° C.

The following compounds of formula Ix (see Table C), i.e. compounds of general formula I where $A^1$ is 3-Cl-5-CF$_3$-2-pyridyl and L is —C(=O)NHCH(R$^1$)—, may be prepared by methods analogous to those of Example 5.

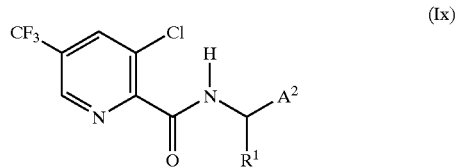

(Ix)

TABLE C

| Cmp | R$^1$ | A$^2$ | m.p. (° C.) |
|---|---|---|---|
| 201 | H | 2,6-diF-phenyl | 137 |
| 202 | Me | 2,6-diF-phenyl | 97 |
| 203 | H | 2-Cl-phenyl | 100–7 |
| 204 | H | 2,6-diCl-phenyl | 114–6 |
| 205 | Me | 2-Cl-phenyl | 120 |
| 206 | Me | phenyl | 88 |
| 207 | Me | 4-Cl-phenyl | 129 |
| 208 | Me | 4-Br-phenyl | 139 |
| 209 | Me | 3,4-diF-phenyl | 127 |
| 210 | Me | [methylenedioxyphenyl] | 123 |
| 211 | Me | 4-CF$_3$O-phenyl | 95 |
| 212 | Me | 3-CF$_3$O-phenyl | 114 |
| 213 | Me | [tetrahydronaphthyl] | 125 |
| 214 | Me | [benzodioxanyl] | 129 |
| 215 | H | 4-tolyl | 113 |

EXAMPLE 6

[3-Chloro-5-(trifluoromethyl)-2-pyridyl]methyl 2-chlorobenzoate Compound 301

To a solution of 2-chlorobenzoic acid (0.1 g) in dimethylformamide was added cesium carbonate (0.1 g) and the resulting solution was stirred for 1 hour. 3-Chloro-2-(chloromethyl)-5-trifluoromethyl pyridine (0.14 g) was added and stirring was continued for a further 48 hours. The solution was diluted with diethyl ether (10 ml) and washed with water (10 ml). The organic phase was separated, dried and evaporated to give a crude product. Silica gel chromatography (petrol/diethyl ether 7:3) gave the title compound, $^1$H N.M.R (CDCl$_3$) δ(ppm) 5.6 (2H, s), 7.3 (1H, m), 7.4 (2H, m) 7.87 (1H, s), 7.88 (1H, d) and 8.8 (1H, s).

The following compounds of formula Iw (see Table D), i.e. compounds of general formula I where $A^1$ is 3-Cl-5-CF$_3$-2-pyridyl and L is —CH$_2$O(C=O)—, may be prepared by methods analogous to those of Example 6.

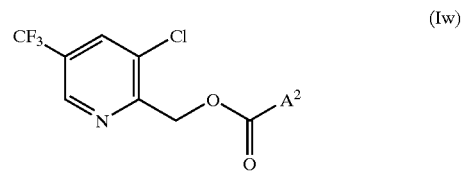

(Iw)

TABLE D

| Cmp | A$^2$ | m.p./° C. |
|---|---|---|
| 301 | 2-Cl-phenyl | oil |
| 302 | 2,6-diCl-phenyl | 93–5 |

EXAMPLE 7

[3-Chloro-5-(trifluoromethyl)-2-pyridyl]methyl(2,4-dichlorobenzyl) ether (Compound 401)

To a solution of 2,4-dichlorobenzyl alcohol (0.27 g) in tetrahydrofuran under nitrogen was added sodium hydride (1.1 equivalents) portionwise. The resulting solution was stirred at room temperature for 1 hour before the addition of 3-chloro-2)-chloromethyl)-5-trifluoromethyl pyridine (0.35 g) in tetrahydrofuran dropwise. The solution was then stirred at room temperature for 16 hours. The solution was treated with a tetrahydrofuran/methanol solution and the solvent then evaporated. The residue was partitioned between water and ethyl acetate, the organic phase was isolated, washed with brine, dried and evaporated to yield the crude product. Silica gel chromatography (petrol/ethyl acetate 95:5) furnished the title compound, $^1$H N.M.R (CDCl$_3$) δ(ppm) 4.8 (2H, s), 4.9 (2H, s), 7.3 (1H, m), 7.4 (1H, m), 7.5(1H, m) 8.0(1H, s) and 8.8(1H, m).

The following compounds of formula Iv (see Table E), i.e. compounds of general formula I where $A^1$ is 3-Cl-5-CF$_3$-2-pyridyl and L is —CH$_2$OCH$_2$—, may be prepared by methods analogous to those of Example 7.

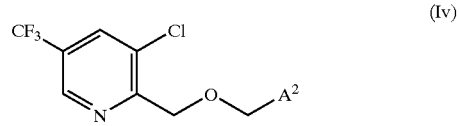

(Iv)

TABLE E

| Cmp | A$^2$ | m.p./° C. |
|---|---|---|
| 401 | 2,4-diCl-phenyl | oil |
| 402 | 2,6-diCl-phenyl | oil |

The $^1$H N.M.R. data of those compounds in Table E which were not solid at room temperature are presented below.
Compound 402

$^1$H N.M.R (CDCl$_3$) δ(ppm) 4.9 (2H, s), 5.0 (2H, s), 7.2 (1H, m), 7.3 (2H, m), 8.0 (1H, s), 8.8 (1H, s).

EXAMPLE 8

N-[2-Chloro-5-(tifluoromethyl)-2-pyridyl]-N'-(2,6-dichlorophenyl)urea (Compound 501)

A solution of triphosgene (1.1 g) in dichloromethane (20 ml) was added over 30 minutes at room temperature to a stirred solution of 2-amino-3-chloro-5-(trifluoromethyl) pyridine (1.96 g) and triethylamine (2 ml) in dichloromethane (35 ml). After 15 minutes a solution of 2,6-dichloroaniline (1.62 g) and triethylamine (2 ml) in dichloromethane (20 ml) was added rapidly and the resulting mixture stirred for 30 minutes before solvent evaporation. The residue was suspended in ethyl acetate and the solid filtered off. The filtrate was washed with potassium hydrogen sulfate solution, sodium bicarbonate solution and then brine. Drying (MgSO$_4$) and solvent evaporation yielded the crude product, which was purified by silica gel chromatography to give the title compound, m.p. 155–8° C.

The following compounds of formula Iu (see Table F), i.e. compounds of general formula I where A$^1$ is 3-Cl-5-CF$_3$-2-pyridyl and L is —NHC(=O)NH—, may be prepared by methods analogous to those of Example 8.

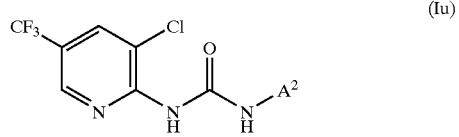

(Iu)

TABLE F

| Cmp | A$^2$ | m.p./° C. |
|---|---|---|
| 501 | 2,6-diCl-phenyl | 155-8 |
| 502 | phenyl | 173-5 |
| 503 | 2-NO$_2$-phenyl | 178-80 |

EXAMPLE 9

3-[3-Chloro-5-(trifluoromethyl)-2-pyridyl]-1-(2-nitrophenyl)-2-propen-1-one (Compound 601)

Sodium hydroxide (0.55 g) was dissolved in water (5 ml) and the resulting solution was diluted with ethanol (3 ml). 2-Nitroacetophenone (1.8 g) was added at 20° C., and the solution was stirred for 5 minutes. 3-Chloro-5-(trifluoromethyl)pyridine-2-carboxaldehyde (2.25 g) was added and stirring was continued for 16 hours. The solution was acidified with acetic acid, the organic layer separated, dried over magnesium sulfate, filtered and evaporated to give a brown oil. Silica gel column chromatography, followed by recrystallisation (petrol) afforded the title compound, 88–9° C.

EXAMPLE 10

3-Chloro-5-(trifluoromethyl)-2-pyridinecarbaldehyde 2-(2-nitrophenyl)hydrazone (Compound 701)

A mixture of 3-chloro-5-(trifluoromethyl)pyridine-2-carboxaldehyde (1.05 g) and 2-nitrophenylhydrazine (0.76 g) in ethanol (75 ml) was heated at reflux for 2.5 hours and then allowed to cool to room temperature overnight. The resulting orange solid was isolated by filtration and recrystallised (petrol) to afford the title compound as admixture of isomers, m.p. 127–35° C.

EXAMPLE 11

[3-Chloro-5-(trifluoromethyl)-2-pyridyl](diphenylmethylene)amino]methyl cyanide (Compound 803)

To a suspension of 60% sodium hydride (4.0 g) in dimethylformamide under a nitrogen atmosphere at 0° C. was added a solution of [(diphenylmethylene)amino]methyl cyanide (11.1 g) in dimethylformamide dropwise, whilst maintaining the temperature between 0° C. and 2° C. The solution was stirred at 0° C. for 1 hour. 2,3-Dichloro-5-trifluoromethylpyridine (7 ml) in dimethylformamide was added dropwise and the mixture stirred for 30 minutes at 0° C. before warming to ambient temperature over 3 hours. The mixture was cooled to 10° C., ethanol (3 ml) added and the solution stirred for 15 minutes. The reaction mixture was then poured as a thin stream into a vigorously stirred mixture of diethyl ether (500 ml) and ammonium chloride solution (500 ml). The organic layer was separated and washed with ammonium chloride solution (2×150 ml), dried, filtered and evaporated to give a residue.

Silica gel chromatography (diethyl ether:petrol 5:95) gave the title product as a pale brown solid, m.p. 108–10° C.

The following compounds of formula It (see Table G), i.e. compounds of general formula I where A$^1$ is 3-Cl-5-CF$_3$-2-pyridyl, L is —CH(R$^1$)N=C(Ph)—, and A$^2$ is phenyl may be prepared by methods analogous to those of Example 11.

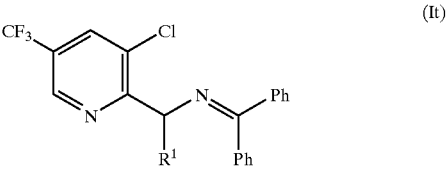

(It)

TABLE G

| Cmp | R$^1$ | m.p./° C. |
|---|---|---|
| 801 | CH$_2$CN | 82-4 |
| 802 | CO$_2$Et | oil |
| 803 | CN | 108-10 |

The mass spectral data of the compound in Table G which was not solid at room temperature is presented below.
Compound 802
  m/z (EI) 373 (M$^+$ —CO$_2$Et)

EXAMPLE 12

1-Biphenylyl-1-ethanone O-1-[3-chloro-5-(trifluoromethyl)-2-pyridyl] oxime (Compound 936)

To 4-acetylbiphenyl oxime (2.5 g) in dimethylformamide (13 ml) under a nitrogen atmosphere was added sodium hydride (0.5 g) portionwise with cooling. The resulting mixture was stirred at 40° C. for 20 minutes until the formation of a suspension occurred. 2,3-Dichloro-5-(trifluoromethyl)pyridine (2.5 g) in dimethylformamide (7 ml) was then added and the resulting mixture stirred for 18 hours at room temperature. The mixture was treated with isopropanol (2 ml) and stirred for 5 minutes before pouring into an ice water/brine solution (300 ml). The resulting precipitate was extracted with diethyl ether (2×125 ml), the organics washed with water, dried, filtered and evaporated to give a solid which on trituration (diethyl ether) and recrystallisation (toluene) yielded the title compound, m.p. 122° C.

Preparation of Starting Material

4-Acetylbiphenyl Oxime

To a suspension of 4-acetylbiphenyl (25.4 g) in ethanol (230 ml) and water (4 ml) under a nitrogen atmosphere was added hydroxylamine hydrochloride (14.5 g) in water (25 ml) followed by 50% aqueous potassium hydroxide solution (40 g). The resulting mixture was heated at reflux for 18 hours and then cooled to room temperature. The mixture was added to ice/water (500 ml) and acidified to pH 2 to give a precipitate. The solid was filtered off, washed with water until the washings were at pH 6 and then recrystallised from ethanol to give the title compound.

following compounds of formula Is (see Table H), i.e. compounds of general formula I where L is —O—N=(R$^1$)—, may be prepared by methods analogous to those of Example 12. The crossed bond in Is indicates that the compounds may exist as cis or trans isomers about the double bond. Isolation of both isomers was possible for some compounds.

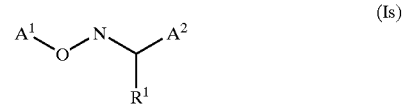 (Is)

TABLE H

| Cmp | A$^1$ | R$^1$ | A$^2$ | m.p. (° C.) |
|---|---|---|---|---|
| 901 | 3-Cl-5-CF$_3$-2-pyridyl | Me | 2-Cl-phenyl | 96–7 |
| 902 | 3-Cl-5-CF$_3$-2-pyridyl | H | 4-pyridyl | 205–6 |
| 903 | 3-Cl-5-CF$_3$-2-pyridyl | Me | 3-(2-Cl-4-CF$_3$-phenoxy)phenyl | 65–7 |
| 904 | 3-Cl-5-CF$_3$-2-pyridyl | H | 2-Cl-6-F-phenyl | 119–23 |
| 905 | 3-Cl-5-CF$_3$-2-pyridyl | H | 2,6-diCl-phenyl | 136–7 |
| 906 | 3-Cl-5-CF$_3$-2-pyridyl | Me | 1-Me-2-pyrolyl | 88–9 |
| 907 | 3-Cl-5-CF$_3$-2-pyridyl | Me | 2-tolyl | oil |
| 908 | 3-Cl-5-CF$_3$-2-pyridyl | Me | 2-tolyl | oil |
| 909 | 3-Cl-5-CF$_3$-2-pyridyl | Me | 3-CF$_3$-phenyl | oil |
| 910 | 3-Cl-5-CF$_3$-2-pyridyl | Me | 2-CF$_3$-phenyl | oil |
| 911 | 3-Cl-5-CF$_3$-2-pyridyl | Me |  | oil |
| 912 | 3-Cl-5-CF$_3$-2-pyridyl | tBu | 2-pyridyl | oil |
| 913 | 3-Cl-5-CF$_3$-2-pyridyl | Me | 2-thienyl | oil |
| 914 | 3-Cl-5-CF$_3$-2-pyridyl | H | 4-MeO-phenyl | oil |
| 915 | 3-Cl-5-CF$_3$-2-pyridyl | Me | 2,4-xylyl | oil |
| 916 | 3-Cl-5-CF$_3$-2-pyridyl | H | 6-Me-2-pyridyl | oil |
| 917 | 3-Cl-5-CF$_3$-2-pyridyl | Me | 2-naphthyl | oil |
| 918 | 3-Cl-5-CF$_3$-2-pyridyl | Me | 1-naphthyl | oil |
| 919 | 3-Cl-5-CF$_3$-2-pyridyl | H | 4-EtO-phenyl | oil |
| 920 | 3-Cl-5-CF$_3$-2-pyridyl | H | 2-tolyl | oil |
| 921 | 3-Cl-5-CF$_3$-2-pyridyl | H | 2-MeO-phenyl | oil |
| 922 | 3-Cl-5-CF$_3$-2-pyridyl | Et | phenyl | oil |
| 923 | 3-Cl-5-CF$_3$-2-pyridyl | H | 3-NO$_2$-phenyl | 116–8 |
| 924 | 3-Cl-5-CF$_3$-2-pyridyl | CF$_3$ | 2-tolyl | oil |
| 925 | 3-Cl-5-CF$_3$-2-pyridyl | (EtO)$_2$P(=O)— | cyclohexyl | oil |
| 926 | 3-Cl-5-CF$_3$-2-pyridyl | —CN | phenyl | 76 |
| 927 | 3-Cl-5-CF$_3$-2-pyridyl | Me | phenyl | oil |
| 928 | 3-Cl-5-CF$_3$-2-pyridyl | H | 2-NO$_2$-phenyl | oil |
| 929 | 3-Cl-5-CF$_3$-2-pyridyl | H | 2-Cl-phenyl | 87 |
| 930 | 3-Cl-5-CF$_3$-2-pyridyl | H | 3-tolyl | oil |
| 931 | 3-Cl-5-CF$_3$-2-pyridyl | H | 3-pyridyl | oil |
| 932 | 3-Cl-5-CF$_3$-2-pyridyl | H | 3-pyridyl | 137–8 |
| 933 | 3-Cl-5-CF$_3$-2-pyridyl | H | 1-naphthyl | 85–90 |
| 934 | 3,5-diCl-2-pyridyl | Me | 2-Cl-phenyl | 127 |
| 935 | 3,5-diCl-2-pyridyl | Me | 2-Cl-phenyl | 70–1 |
| 936 | 3-Cl-5-CF$_3$-2-pyridyl | Me | biphenylyl | 122 |
| 937 | 3-Cl-5-CF$_3$-2-pyridyl | —CN | 2,6-diCl-phenyl | 128–9 |
| 938 | 3-Cl-5-CF$_3$-2-pyridyl | —CN | 2,6-diCl-phenyl | 71–2 |
| 939 | 3-Cl-5-CF$_3$-2-pyridyl | —CN | 2-CN-phenyl | 139–43 |
| 940 | 3-Cl-5-CF$_3$-2-pyridyl | —CN | 2-Cl-phenyl | 83–4 |
| 941 | 3-Cl-5-CF$_3$-2-pyridyl | —CN | 2-Cl-phenyl | 88 |
| 942 | 3-Cl-5-CF$_3$-2-pyridyl | Me | 2-MeSO$_2$-phenyl | oil |
| 943 | 3-Cl-5-CF$_3$-2-pyridyl | Ph | 2-naphthyl | oil |
| 944 | 3-Cl-5-CF$_3$-2-pyridyl | Me | 6-MeO-2-naphthyl | oil |
| 945 | 3-Cl-5-CF$_3$-2-pyridyl | Me | 4-F-1-naphthyl | oil |
| 946 | 3-Cl-5-CF$_3$-2-pyridyl | Me | 4-cyclohexyl-phenyl | oil |

TABLE H-continued

| Cmp | A¹ | R¹ | A² | m.p. (° C.) |
|---|---|---|---|---|
| 947 | 3-Cl-5-CF$_3$-2-pyridyl | Me | 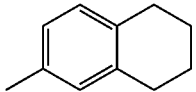 | oil |
| 948 | 3-Cl-5-CF$_3$-2-pyridyl | Pr | 4-Cl-phenyl | oil |
| 949 | 3-Cl-5-CF$_3$-2-pyridyl | Me | cyclohexyl | oil |
| 950 | 3-Cl-5-CF$_3$-2-pyridyl | Me | 4-PhO-phenyl | oil |
| 951 | 3-Cl-5-CF$_3$-2-pyridyl | Me | 2,5-diMe-3-furyl | oil |
| 952 | 3-Cl-5-CF$_3$-2-pyridyl | Me | 3,5-diMe-isothiazol-4-yl | oil |
| 953 | 3-Cl-5-CF$_3$-2-pyridyl | Et | 2,4-diCl-phenyl | oil |
| 954 | 3-Cl-5-CF$_3$-2-pyridyl | Me | 2,3-diCl-phenyl | oil |
| 955 | 3-Cl-5-CF$_3$-2-pyridyl | —CN | 2-pyridyl | oil |
| 956 | 3-Cl-5-CF$_3$-2-pyridyl | CF$_3$ | 2-thienyl | oil |
| 957 | 3-Cl-5-CF$_3$-2-pyridyl | Me | 4-pyridyl | oil |
| 958 | 3-Cl-5-CF$_3$-2-pyridyl | 4-Cl-phenyl | 4-Cl-phenyl | oil |

$^1$H N.M.R or mass spectral data of those compounds in Table H which were not solid at room temperature are presented below.

Compound 907
 $^1$H N.M.R (CDCl$_3$) δ (ppm) 2.4 (6H, s), 7.2–7.4 (4H, m), 7.95 (1H, s), 8.45 (1H, s).
Compound 908
 $^1$H N.M.R (CDCl$_3$) δ (ppm) 2.3 (3H), 2.4 (3H0, 7.1 (1H), 7.3 (3H, m), 7.8 (1H), 8.45 (1H).
Compound 909
 m/z (EI) 382 (M$^+$).
Compound 910
 $^1$H N.M.R (CDCl$_3$) δ (ppm) 2.5 (3H), 7.45 (1H, d), 7.5–7.7 (2H, m), 7.75 (1H, d), 8.0 (1H, d), 8.5 (1H, d).
Compound 911
 $^1$H N.M.R (CDCl$_3$) δ (ppm) 0.8 (t), 1.15 (d), 1.4 (quintet), 2.0 (s), 23 (s), 3.65 (dd), 7.7 (m), 7.95 (m).
Compound 912
 m/z (EI) 357 (M$^+$).
Compound 913
 m/z (EI) 320 (M$^+$).
Compound 914
 m/z (EI) 330 (M$^+$).
Compound 915
 m/z (EI) 342 (M$^+$).
Compound 916
 m/z (EI) 315 (M$^+$).
Compound 917
 m/z (EI) 364 (M$^+$).
Compound 918
 m/z (EI) 364 (M$^+$).
Compound 919
 m/z (EI) 344 (M$^+$).
Compound 920
 $^1$H N.M.R (CDCl$_3$) δ (ppm) 2.35 (s), 2.5 (s), 7.4 (d), 7.8 (m), 7.9 (d).
Compound 921
 $^1$H N.M.R (CDCl$_3$) δ (ppm) 3.9 (3H, m), 6.9–7.05 (2H, m), 7.5–7.75 (2H, m), 7.95 (1H, d), 8.0 (1H, d), 8.5 (1H, d), 9.1 (1H).
Compound 922
 m/z (EI) 328 (M$^+$).
Compound 924
 m/z (EI) 382 (M$^+$).
Compound 925
 $^1$H N.M.R (CDCl$_3$) δ (ppm) 1.3 (m), 2.7 (m), 4.2 (m), 7.75 (d), 7.95 (d).
Compound 927
 m/z (EI) 314 (M$^+$).
Compound 928
 m/z (EI) 345 (M$^+$).
Compound 930
 $^1$H N.M.R (CDCl$_3$) δ (ppm) 2.35 (d), 7.25 (m), 7.5 (d), 7.9 (d), 8.5 (d), 8.65 (s).
Compound 931
 m/z (EI) 301 (M$^+$).
Compound 942
 $^1$H N.M.R (CDCl$_3$) δ (ppm) 2.6 (3H, s), 3.05 (3H, s), 8.0 (5H, m), 8.5 (1H, s).
Compound 943
 $^1$H N.M.R (CDCl$_3$) δ (ppm) 7.4–7.6 (7H, m), 7.8–8.0 (6H, m), 8.5 (1H, d).
Compound 944
 m/z (EI) 393 (M$^+$).
Compound 945
 $^1$H N.M.R (CDCl$_3$) δ (ppm) 2.7 (3H, s), 7.15 (1H, dd), 7.5–7.65 (3H, m), 7.95 (1H, d), 8.1–8.25 (2H, m), 8.5 (1H, d).
Compound 946
 m/z (EI) 396 (M$^+$).
Compound 947
 m/z (EI) 368 (M$^+$).
Compound 948
 m/z (EI) 376 (M$^+$).
Compound 949
 $^1$H N.M.R (CDCl$_3$) δ (ppm) 0.1–1.5 (5H, m), 1.7–1.9 (5H, m), 2.6 (1H, t), 8.0 (1H, m), 8.55 (1H, m).
Compound 950
 m/z (EI) 406 (M$^+$).
Compound 951
 m/z (EI) 332 (M$^+$).
Compound 952
 m/z (EI) 349 (M$^+$).
Compound 953
 $^1$H N.M.R (CDCl$_3$) δ (ppm) 1.4 (3H, t), 3.0 (2H, q), 7.2 (3H, t) isomer, 7.3 (1H, d), 7.55 (1H, dd), 8.0 (1H, d, m), 8.55 (1H, d, m).
Compound 954
 $^1$H N.M.R (CDCl$_3$) δ (ppm) 2.5 (3H, m), 7.2–7.4 (2H, m), 7.5 (1H, d), 7.9 (1H), 8.4 (1H).
Compound 955
 $^1$H N.M.R (CDCl$_3$) δ (ppm) 2.6 (s), 4.8 (s), 7.25 (t), 7.5 (dd), 7.9 (m), 8.05 (d), 8.15 (d), 8.5 (s), 8.8 (d).

Compound 956
  m/z (EI) 374 (M$^+$).
Compound 957
  m/z (EI) 314 (M$^+$).
Compound 958
  $^1$H N.M.R (CDCl$_3$) δ (ppm) 7.35–7.6 (8H, m), 7.9 (1H), 8.5 (1H).

EXAMPLE 13

N-(3-Chloro-5-trifluoromethyl-2-pyridyloxy)-1-naphthalenecarboxamide (Compound 1012)

A mixture of 1-naphthoic acid (0.46 g) and carbonyldiimidazole (0.44 g) in tetrahydrofuran (40 ml) was stirred for 16 hours under a nitrogen atmosphere. The product from stage b) (0.57 g) was then added, and the mixture stirred for 5 days. The solution was poured into saturated brine solution and the organic portion extracted with ethyl acetate (x3), dried (MgSO$_4$), filtered and evaporated. The residue was purified by silica gel chromatography (ethyl acetate/petrol) and triturated (diisopropyl ether) to give the title product, m.p. 198–9° C.

Preparation of Starting Materials a) 2-{[3-Chloro-5-(trifluoromethyl)-2-pyridyl]oxy}-1,3-isoindolinedione 2,3-Dichloro-5-trifluoromethylpyridine (50.0 g) was added over 5 minutes to a stirred solution of N-hydroxyphthalimide (37.5 g) and triethylanine (25.8 g) in acetone (750 ml). The mixture was refluxed for 8 hours and allowed to stand at room temperature for 16 hours. The solution was filtered and the filtrate evaporated to yield a solid which was partitioned between ethyl acetate and sodium bicarbonate solution. The organic fraction was isolated and the aqueous material re-extracted using further portions of ethyl acetate. The combined organic extracts were washed with water, dried, filtered and evaporated to give the crude product. The residue was triturated with diisopropyl ether to furnish the title compound as a white solid.

b) O-[3-Chloro-5-(trifluoromethyl)-2-pyridyl]hydroxylamine

Hydrazine monohydrate (1.7 g) was added to a solution of the product from stage a) (11.3 g) in tetrahydrofuran (200 ml) and the mixture stirred for 16 hours. The mixture was then filtered and the residual solid washed with a small volume of tetrahydrofuran and ethyl acetate, then four times with a 0.02M solution of sodium hydroxide saturated with sodium chloride. The combined aqueous layers were extracted with dichloromethane (x2) and the combined organic extracts dried, filtered and evaporated to give the title compound.

EXAMPLE 14

N-(3-Chloro-5-trifluoromethyl-2-pyridyloxy)-N-methyl-1-naphthalenecarboxamide (Compound 1017)

Iodomethane (0.82 g) was added to a stirred solution of the product from Example 13 (Compound 1012) (1.93 g) and potassium tert-butoxide (0.61 g) in tetahydrofuran (50 ml). The reaction mixture was stirred for 48 hours. The solvent was evaporated and the residue partitioned between ethyl acetate and saturated aqueous ammonium chloride. The aqueous layer was separated and extracted with 3 portions of ethyl acetate. The combined organic phases were dried, filtered and evaporated to give a residue which was purified by silica gel chromatography (ethyl acetate/petrol) to give the title compound, m/z (EI) 380 (M$^+$).

The following compounds of formula Ir (see Table J), i.e. compounds of general formula I where A$^1$ is 3-Cl-5-CF$_3$-2-pyridyl and L is —O—N(R$^3$)C(=O)—, may be prepared by methods analogous to those of Examples 13 and 14.

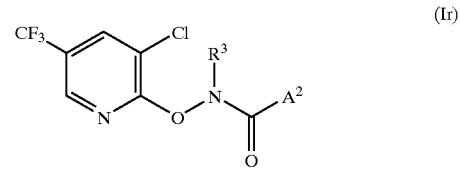

(Ir)

TABLE J

| Cmp | R$^3$ | A$^2$ | m.p. (° C.) |
|---|---|---|---|
| 1001 | H | 5-Me-2-pyrazinyl | 202–6 |
| 1002 | H | 4-tolyl | 190–3 |
| 1003 | H | 2-Cl-4-CF$_3$-pyrimidin-5-yl | 204–5 |
| 1004 | H | 4-Cl-phenyl | 191–3 |
| 1005 | H | 2-NO$_2$-5-(2-Cl-4-CF$_3$-phenoxy)-phenyl | 168–70 |
| 1006 | H | 3,5-diMe-4-isoxazolyl | 108–11 |
| 1007 | H | 2,4-diMe-5-thiazolyl | 152–5 |
| 1008 | H | 4,6-diMeO-2-(α,α-diMe-4-Cl-benzyl)-pyrimidin-5-yl | 124–5 |
| 1009 | H | 5-(3,5-diCl-phenoxy)-2-furyl | 120–2 |
| 1010 | H | 6-MeO-3-pyridyl | 157–9 |
| 1011 | H | 2-naphthyl | 180 |
| 1012 | H | 1-naphthyl | 198–9 |
| 1013 | H | 2-Cl-phenyl | 170 |
| 1014 | H | 3-quinolinyl | 238–9 |
| 1015 | H | ![structure] | oil |
| 1016 | H | 4-morpholinyl-3-NO$_2$-phenyl | 217–8 |
| 1017 | Me | 1-naphthyl | oil |
| 1018 | H | 1-naphthyl | 218–20 |
| 1019 | H | 2,6-diCl-phenyl | 246–7 |

The mass spectral data of the compounds in Table J which were not solid at room temperature are presented below.
Compound 1015
  m/z (EI) 412 (M$^+$).
Compound 1017
  m/z (EI) 380 (M$^+$).

EXAMPLE 15

2-Methyl-1,2,3,4-tetrahydro-1-naphthalenone O-1-[3-chloror-5-(trifluoromethyl)-2-pyridyl]oxime (Compound 1101)

The starting material (0.58 g) was dissolved in tetrahydrofuran (5 ml) and to this was added potassium tert-butoxide (0.42 g) dissolved in tetrahydrofuran (5 ml). The mixture was stirred overnight and a solution of 2,3-dichloro-5-trifluoromethyl pyridine (0.72 g) in tetrahydrofuran (2 ml) was added. The mixture was stirred for 48 hours at room temperature, then the solvent was evaporated. The residue was partitioned between ethyl acetate and water. The organic layer was isolated, dried, filtered and evaporated to yield the title product as a light yellow gum, m/z (EI) 354 (M$^+$).

a) 2-Methyl-1,2,3,4-tetrahydro-1-naphthalenone oxime

To a solution of 2-methyl-1-tetralone (3.20 g) in methanol (5 ml) was added hydroxylamine hydrochloride (1.81 g) in methanol (15 ml) and triethylamine (2.63 g). The mixture was stirred at 65° C. for 5 hours, allowed to cool and stand at room temperature for 16 hours. The solvent was evaporated and water added to the residue. The product was extracted with ethyl acetate (3 portions) and the combined extracts were dried, filtered and evaporated to give an orange oil. On standing this separated into two layers. The top layer was removed and the bottom layer slowly solidified to give the title product as an orange solid.

The following compounds of formula Iq (see Table K), i.e. compounds of general formula I where $A^1$ is 3-Cl-5-$CF_3$-2-pyridyl and L is —O—N=C($R^1$)—, wherein $R^1$ and $A^2$, together with the interconnecting atoms forms a 5- or 6-membered ring, may be prepared by methods analogous to those of Example 15.

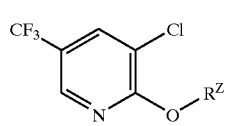

(Iq)

TABLE K

| Cmp | $R^Z$ | m.p. (° C.) |
|---|---|---|
| 1101 | (2-Me-tetrahydronaphthalen-1-ylidene) | oil |
| 1102 | (7-OMe-tetrahydronaphthalen-1-ylidene) | oil |
| 1103 | (7-NO₂-tetrahydronaphthalen-1-ylidene) | oil |
| 1104 | (chroman-4-ylidene) | oil |
| 1105 | (6-Cl-chroman-4-ylidene) | oil |

TABLE K-continued

| Cmp | $R^Z$ | m.p. (° C.) |
|---|---|---|
| 1106 | (thiochroman-4-ylidene) | oil |
| 1107 | (decahydronaphthalen-1-ylidene) | oil |
| 1108 | (6-OMe-octahydronaphthalen-1-ylidene) | oil |
| 1109 | (1-Me-2-oxoindolin-3-ylidene) | oil |
| 1110 | (5-Cl-1-Me-2-oxoindolin-3-ylidene) | oil |

Those compounds in Table K which do not have discrete melting points have the following characteristic mass spectral data.

Compound 1101
  m/z (EI) 354 ($M^+$).
Compound 1102
  m/z (EI) 370 ($M^+$).
Compound 1103
  m/z (EI) 385 ($M^+$).
Compound 1104
  m/z (EI) 342 ($M^+$).
Compound 1105
  m/z (EI) 376 ($M^+$).
Compound 1106
  m/z (EI) 358 ($M^+$).
Compound 1107
  m/z (EI) 346 ($M^+$).
Compound 1108
  m/z (EI) 370 ($M^+$).
Compound 1109
  m/z (EI) 355 ($M^+$).
Compound 1110
  m/z (EI) 389 ($M^+$).

EXAMPLE 16

2-{[2-(3-Bromo-4-methoxyphenyl)-1H-1-imidazolyl]methyl}-3-chloro-5-(trifluoromethyl) pyridine (Compound 1201)

To a solution of 2)-3-bromo-4-methoxyphenyl)-1H-imidazole (0.5 g) in tetrahydrofuran was added sodium hydride (0.08 g). After 30 minutes 3-chloro-2-(chloromethyl)-5-trifluoromethyl pyridine (0.46 g) was added and the solution heated until the reaction was complete. The reaction mixture was cooled, poured onto water and the organic phase extracted using dichloromethane, dried and evaporated to yield the crude product as an orange gum. Silica gel column chromatography yielded a gum which was further treated with diisopropyl ether and filtered. Evaporation of the filtrate afforded the title compound, m/z (APCI) 445 (M⁻).

2-(3-Bromo-4-methoxyphenyl)imidazole was synthesised from 3-bromo-4-methoxybenzonitrile using a method known to the skilled chemist.

Test Example

Compounds were assessed for activity against one or more of the following:

*Phytophthora infestans*: late tomato blight
*Plasmopara viticola*: vine downy mildew
*Erysiphe graminis f.* sp. *tritici*: wheat powdery mildew
Pyricularia oryzae: rice blast
*Leptosphaeria nodorum*: glume blotch Aqueous solutions or dispersions of the compounds at the desired concentration, including a wetting agent, were applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Phytophthora infestans*: 49, 102, 119, 126, 202, 214, 215, 601, 902, 912, 927, 953, 1101 and 1102.
*Plasmopara viticola*: 7,9, 10, 12, 102, 109, 126, 214, 215, 601, 901, 907, 914, 915, 921, 926–30, 958, 1001 and 1013.
*Erysiphe graminis f.* sp. *tritici*: 501, 901, 906, 913–5, 923, 926–931, 933, 935, 936, 948–50, 952, 954, 1008, 1102, 1104, 1107 and 1108.
*Pyricularia oryzae*: 7, 9, 11, 17, 126, 901, 906, 907, 913, 922, 923, 926–31, 937, 938, 939 and 1001.
*Leptosphaeria nodorum*: 23, 51, 53, 126, 207, 208, 906, 923, 926, 929, 933, 1007 and 1109.

What is claimed is:

1. A method of combating plant fungi at a locus infested or liable to be infested therewith, which comprises applying to the locus a sufficient amount of a phytopathogenie fungicide to combat said plant fungi, said phytopathogenic fungicide comprising a compound of general formula I or salts thereof;

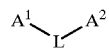
(I)

where $A^1$ is 3-Cl-5-CF$_3$-2-pyridyl;

$A^2$ is optionally substituted heterocyclyl or optionally substituted carbocyclyl; excepted where L is —N(R$_3$)N(R$_4$)C(=O)— or —CH$_2$OCH$_2$—, then A$_2$ can not be a heterocyclyl containing N or O;

L is a 3-atom linker of formula —N(R$_3$)N(R$_4$)C(=X)—;

wherein $A^1$ is attached to the left hand side of linker L;

where $R^1$ and $R^2$, which may be the same or different, are $R^b$, cyano, nitro, halogen, —OR$^b$, —SR$^b$ or optionally substituted amino;

$R^3$ and $R^4$, which may be the same or different, are $R^b$, cyano or nitro;

or any $R^1$, $R^2$, $R^3$ or $R^4$ group, together with the interconnecting atoms, can form a 5- or 6-membered ring with any other $R^1$, $R^2$, $R^3$ or $R^4$, or any $R^1$, $R^2$, $R^3$ or $R^4$ group, together with the interconnecting atoms can form a 5- or 6-membered ring with $A^2$;

X is oxygen, sulfur, N—OR$^b$, or N—(R$^b$)$_2$; and

Y is halogen, —OR$^b$, —SR$^b$, —N(R$^b$)$_2$, —NR$^b$(OR$^b$) or NR$^b$N(R$^b$)$_2$;

wherein $R^b$ is alkyl, alkenyl, alkynyl, carbocyclyl or heterocyclyl, each of which may be substituted; or hydrogen or acyl, or two adjacent $R^b$ groups together with the nitrogen atom to which they are attached may form a 5- or 6-membered ring.

2. A fungicide composition comprising at least one compound as recited in claim 1 in admixture with an agriculturally acceptable diluent or carrier.

\* \* \* \* \*

UNITED STATES PATENT AND TRADEMARK OFFICE
CERTIFICATE OF CORRECTION

PATENT NO. : 6,939,882 B1
DATED : September 6, 2005
INVENTOR(S) : Cooke et al.

It is certified that error appears in the above-identified patent and that said Letters Patent is hereby corrected as shown below:

Title page,
Item [73], Assignee, "Aventis Cropsciences GmbH (DE)" should be changed to
-- Aventis Cropscience GmbH (DE) --.

Column 30,
Lines 22-24, delete "-$N(R_3)N(R_4)C(=O)$-or-$CH_2OCH_2$-, then $A_2$ can not be a heterocyclyl containing N or O" and insert -- -$N(R^1)N(R^4)C(=O)$ then $A^2$ can not be a heterocyclyl containing N or O --;
Line 27-29, delete "where $R^1$ and $R^2$, which may be the same or different, are $R^b$, cyano, nitro, halogen, -$OR^b$, -$SR^b$ or optionally substituted amino;".
Lines 31-37, delete "$R^3$ and $R^4$, which may be the same or different, are $R^b$, cyano or nitro; or any $R^1$, $R^2$, $R^3$ or $R^4$ group, together with the interconnecting atoms, can form a 5- or 6-membered ring with any other $R^1$, $R^2$, $R^3$ or $R^4$, or any $R^1$, $R^2$, $R^3$ or $R^4$ group, together with the interconnecting atoms can form a 5- or 6-membered ring with $A^2$" and insert -- $R^3$ and $R^4$, which may be the same or different, are $R^b$, cyano, nitro or together with the interconnecting atoms can form a 5- or 6-membered ring with $A^2$ --;
Lines 40-41, delete "y is halogen, -$OR^b$, -$SR^b$, -$N(R^b)_2$, -$NR^b(OR^b)$ or $NR^bN(R^b)_2$;".

Signed and Sealed this

Twenty-first Day of February, 2006

JON W. DUDAS
*Director of the United States Patent and Trademark Office*